United States Patent
Li et al.

(10) Patent No.: US 11,285,302 B2
(45) Date of Patent: Mar. 29, 2022

(54) GUIDEWIRE-GUIDING DEVICE ASSEMBLY

(71) Applicant: BEIJING ANGEL-REACH MEDICAL TECHNICAL CO., LTD., Beijing (CN)

(72) Inventors: Lei Li, Beijing (CN); Xiaodong Zhang, Beijing (CN); Jun Jiang, Beijing (CN)

(73) Assignee: BEIJING ANGEL-REACH MEDICAL TECHNICAL CO., LTD., Beijing (CN)

( * ) Notice: Subject to any disclaimer, the term of this patent is extended or adjusted under 35 U.S.C. 154(b) by 399 days.

(21) Appl. No.: 15/778,026

(22) PCT Filed: Oct. 10, 2016

(86) PCT No.: PCT/CN2016/101706
§ 371 (c)(1),
(2) Date: May 22, 2018

(87) PCT Pub. No.: WO2017/107621
PCT Pub. Date: Jun. 29, 2017

(65) Prior Publication Data
US 2018/0344988 A1     Dec. 6, 2018

(30) Foreign Application Priority Data
Dec. 24, 2015  (CN) .......................... 201510991289.2

(51) Int. Cl.
*A61M 25/09*     (2006.01)
*A61M 25/01*     (2006.01)
*A61M 25/00*     (2006.01)

(52) U.S. Cl.
CPC .... *A61M 25/09041* (2013.01); *A61M 25/003* (2013.01); *A61M 25/0071* (2013.01);
(Continued)

(58) Field of Classification Search
None
See application file for complete search history.

(56) References Cited

U.S. PATENT DOCUMENTS

2002/0188166 A1   12/2002  Viole et al.
2002/0188167 A1   12/2002  Viole et al.
(Continued)

FOREIGN PATENT DOCUMENTS

CN       1441654 A        9/2003
CN     201481558 U        5/2010
(Continued)

OTHER PUBLICATIONS

Japanese Patent Office, Office Action Issued in Application No. 2018-528329, dated Jan. 7, 2020, 10 pages. (Submitted with Machine Translation).
(Continued)

*Primary Examiner* — Etsub D Berhanu
*Assistant Examiner* — Aurelie H Tu
(74) *Attorney, Agent, or Firm* — McCoy Russell LLP

(57) ABSTRACT

A guidewire-guiding device, and guidewire-guiding assembly. The device comprises a main guidewire channel and guidewire-guiding channels are respectively arranged in the guiding body. The main guidewire channel and the guidewire-guiding channels respectively pass through the guiding body along axial direction, and in-vivo end openings of the guidewire-guiding channels and the in-vivo end opening of the main guidewire channel are arranged along the axial direction at intervals. The guiding body may be imbedded into a vessel in-vivo via the main guidewire penetrating through the main guidewire channel, and as the in-vivo end openings of the guidewire-guiding channels are arranged along the axial direction at intervals, the to-be-guided guidewires enter the guidewire-guiding channels
(Continued)

while being staggered to the main guidewire on the axial direction, therefore the problem of tanglement of the main guidewire the branch guidewires and other kinds of guidewires may be avoided.

7 Claims, 1 Drawing Sheet

(52) U.S. Cl.
CPC ............ *A61M 25/01* (2013.01); *A61M 25/09* (2013.01); *A61M 2025/004* (2013.01); *A61M 2025/0008* (2013.01); *A61M 2025/0031* (2013.01); *A61M 2025/0034* (2013.01); *A61M 2025/0039* (2013.01)

(56) References Cited

U.S. PATENT DOCUMENTS

| | | | |
|---|---|---|---|
| 2004/0220473 A1* | 11/2004 | Lualdi | A61M 25/09041 600/435 |
| 2006/0184156 A1 | 8/2006 | Jang | |
| 2006/0259009 A1 | 11/2006 | Murray | |
| 2009/0005757 A1* | 1/2009 | Taber | A61M 25/01 604/523 |
| 2010/0030057 A1* | 2/2010 | Gavriely | A61B 1/0684 600/407 |
| 2010/0057020 A1 | 3/2010 | Uretsky | |
| 2013/0253474 A1* | 9/2013 | Farhangnia | A61M 25/0074 604/510 |
| 2013/0304030 A1* | 11/2013 | Gray | A61M 25/09041 604/510 |
| 2015/0173782 A1 | 6/2015 | Garrison et al. | |

FOREIGN PATENT DOCUMENTS

| | | |
|---|---|---|
| CN | 102525699 A | 7/2012 |
| CN | 105617512 A | 6/2016 |
| CN | 205287200 U | 6/2016 |
| EP | 1767238 A1 | 3/2007 |
| EP | 2233168 A1 | 9/2010 |
| JP | 2004528139 A | 9/2004 |
| JP | 2007275372 A | 10/2007 |
| JP | 2007532279 A | 11/2007 |
| JP | 2008539954 A | 11/2008 |
| JP | 2015534873 A | 12/2015 |
| WO | 0170299 A2 | 9/2001 |
| WO | 02072186 A2 | 9/2002 |

OTHER PUBLICATIONS

ISA State Intellectual Property Office of the People's Republic of China, International Search Report Issued in Application No. PCT/CN2016/101706, dated Dec. 28, 2016, WIPO, 6 pages.
"Cloversnare 4-Loop Vascular Retriever," Cook Medical Website, Available Online at https://www.cookmedical.com/data/IFU_PDF/T_VRS_REV3.PDF, Oct. 31, 2007, 1 page.
Japanese Patent Office, Office Action Issued in Application No. 2018-528329, dated Apr. 2, 2019, 14 pages.
European Patent Office, Extended European Search Report Issued in Application No. 16877432.1, dated Aug. 1, 2019, Germany, 8 pages.

* cited by examiner

U.S. Patent  Mar. 29, 2022  US 11,285,302 B2
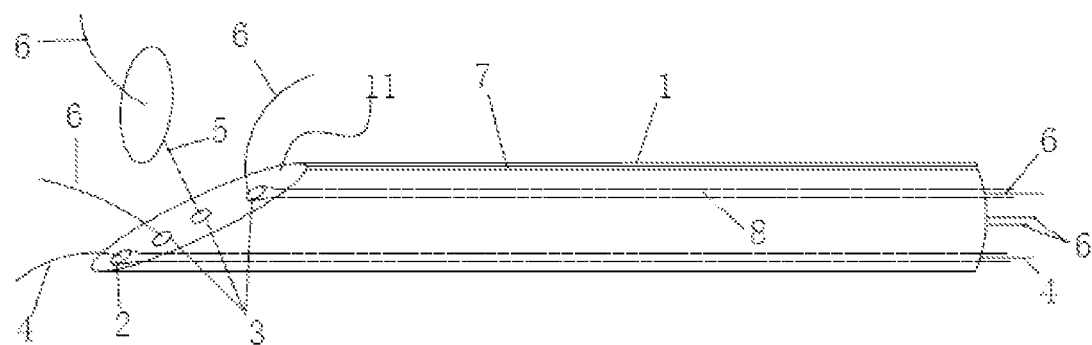
Fig. 1
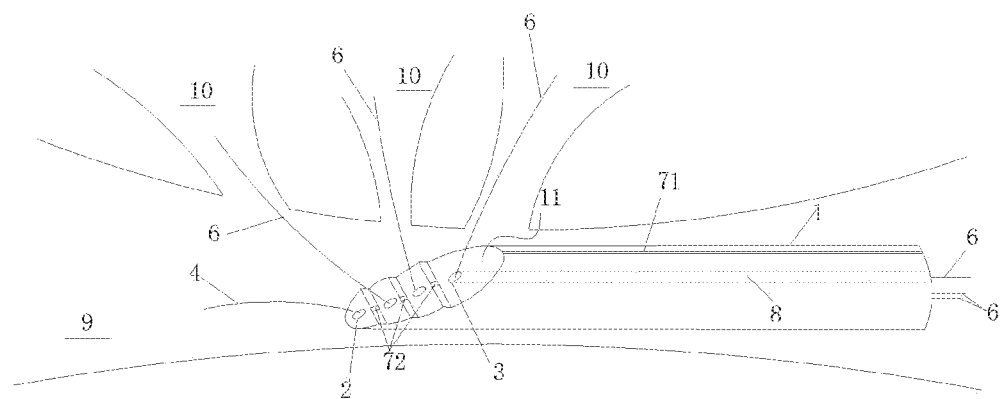
Fig. 3
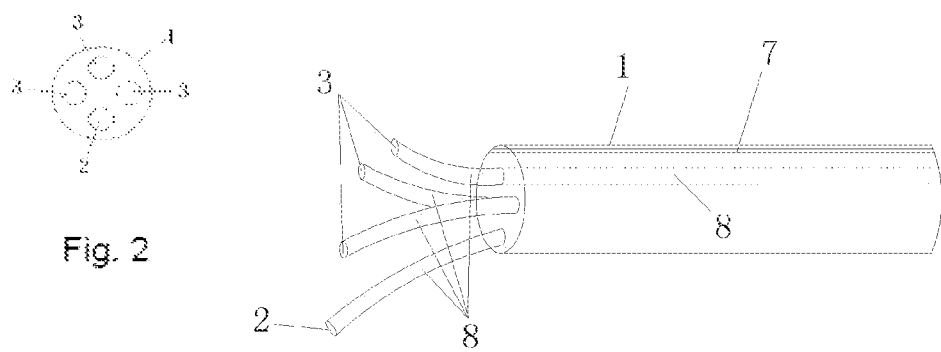
Fig. 2
Fig. 4

GUIDEWIRE-GUIDING DEVICE ASSEMBLY

CROSS-REFERENCE TO RELATED APPLICATIONS

The present application is a U.S. National Phase of International Patent Application Serial No. PCT/CN2016/101706 entitled "GUIDEWIRE-GUIDING DEVICE, AND GUIDEWIRE-GUIDING ASSEMBLY," filed on Oct. 10, 2016. International Patent Application Serial No. PCT/CN2016/101706 claims priority to Chinese Patent Application No. 201510991289.2, filed on Dec. 24, 2015. The entire contents of each of the above-cited applications are hereby incorporated by reference in their entirety for all purposes.

FIELD OF THE INVENTION

The present invention relates to the field of medical devices of interventional therapy, and in particular to a guidewire-guiding device and a guidewire-guiding assembly using the device.

BACKGROUND OF THE INVENTION

With the frequent occurrence of cardiovascular and cerebrovascular diseases, interventional therapy, such as the treatment of vascular stents, is becoming more and more common. Guidewires for guiding and controlling corresponding components in various kinds of interventional therapy are also becoming more and more, if too many guidewires are used in one operation, the guidewires may be tangled with each other in vivo to affect the operation. For example, when a plurality of branch blood vessels are connected to a main blood vessel, the guidewires in the blood vessels are collected in the main blood vessel and extend in vitro, and at this time, the plurality of guidewires are easily tangled in the blood vessel. Therefore, the problem of the tanglement of the plurality of guidewires needs to be solved urgently in the industry.

SUMMARY OF THE INVENTION

One objective of the present invention is to provide a guidewire-guiding device, which effectively avoids the problem of tanglement of guidewires in vivo.

Another objective of the present invention is to provide a guidewire-guiding assembly, which uses the guidewire-guiding device provided by the present invention.

To achieve the above objectives, the present invention provides a guidewire-guiding device, including a guiding body, wherein a main guidewire channel and guidewire-guiding channels are respectively arranged in the guiding body, the main guidewire channel and the guidewire-guiding channels respectively penetrate through the guiding body along an axial direction, and in-vivo end openings of the guidewire-guiding channels and the in-vivo end opening of the main guidewire channel are arranged along the axial direction at intervals.

Preferably, a plurality of guidewire-guiding channels are arranged, and the in-vivo end openings of the plurality of guidewire-guiding channels are arranged along the axial direction at intervals.

Preferably, in-vitro end openings of the plurality of guidewire-guiding channels and the in-vitro end opening of the main guidewire channel are arranged at equal intervals along the circumferential direction of the guiding body.

Preferably, an in-vivo end face of the guiding body is formed into a diagonal plane, and the main guidewire channel and the guidewire-guiding channels are arranged along the diagonal plane to be spaced on the axial direction.

Preferably, the in-vivo end face of the guiding body is formed into a plurality of diagonal planes of a step structure, the plurality of diagonal planes are parallel, and the main guidewire channel and the guidewire-guiding channels are respectively formed on different diagonal planes.

Preferably, the main guidewire channel and the guidewire-guiding channels are respectively formed by pipelines and are coated in the guiding body.

Preferably, the pipelines of the main guidewire channel and the guidewire-guiding channels respectively protrude from the end face of the in-vivo end of the guiding body.

Preferably, a development marking line extending along the axial direction is arranged on the guiding body.

Preferably, a development marking line extending along the axial direction is arranged on the guiding body, the development marking line includes an integral segment and a plurality of sub-segments, the integral segment is deployed on an outer side wall of the guiding body, the plurality of sub-segments are respectively deployed on a plurality of step surfaces of the step structure and are formed on a connecting line between adjacent in-vivo end openings, and the step surfaces are located between the adjacent diagonal planes and are parallel to one another.

Preferably, the in-vivo end openings of the guidewire-guiding channels and/or the main guidewire channel are trumpet-shaped.

Preferably, the section of the guiding body is circular, the diagonal plane is oval, and the in-vivo end opening of the main guidewire channel is arranged in the vicinity of the long axis of the oval.

Preferably, the main guidewire channel is used for guiding a main guidewire penetrating through a main blood vessel, and the guidewire-guiding channels are used for guiding branch guidewires penetrating through branch blood vessels connected to the main blood vessel.

According to another aspect of the present invention, a guidewire-guiding assembly is provided, including the guidewire-guiding device provided by the present invention, and a guidewire catcher stretching in from the in-vitro end openings of the guidewire-guiding channels and stretching out from the in-vivo end openings.

By means of the above technical solution, the guiding body may be imbedded into a blood vessel in vivo via the main guidewire penetrating through the main guidewire channel, the to-be-guided guidewires, for example, the branch guidewires of the branch blood vessels, may be guided into the guidewire-guiding channels via the guidewire catcher. And as the in-vivo end openings of the guidewire-guiding channels are arranged along the axial direction at intervals, the to-be-guided guidewires enter the guidewire-guiding channels while being staggered to the main guidewire on the axial direction, therefore the problem of tanglement of the main guidewire, the branch guidewires and other kinds of guidewires may be avoided, furthermore, the to-be-guided guidewires may be conveniently guided into the guiding body via the guidewire catcher, accordingly the operation is convenient, and the practicability is high.

Other features and advantages of the present invention will be described in detail in the following detailed description.

BRIEF DESCRIPTION OF THE DRAWINGS

The drawings are used to provide a further understanding of the present invention and constitute a part of the specification. The drawings, together with the following specific embodiments, are used to explain the present invention, but are not intended to limit the present invention. In the drawings:

FIG. 1 is a structural schematic diagram of a guidewire-guiding assembly provided by a preferred embodiment of the present invention in a working process;

FIG. 2 is a schematic diagram of a cross section of a guidewire-guiding device provided by a first embodiment of the present invention;

FIG. 3 is a schematic diagram of a cross section of a guidewire-guiding device provided by a second embodiment of the present invention;

FIG. 4 is a schematic diagram of a cross section of a guidewire-guiding device provided by a third embodiment of the present invention.

REFERENCE SIGNS

| 1 | guiding body | 2 | main guidewire channel |
|---|---|---|---|
| 3 | guidewire-guiding channel | 4 | main guidewire |
| 5 | guidewire catcher | 6 | branch guidewire |
| 7 | development marking line | 8 | pipeline |
| 9 | main blood vessel | 10 | branch blood vessel |
| 11 | end face of an in-vivo end | | |

DETAILED DESCRIPTION OF THE EMBODIMENTS

The specific embodiments of the present invention are described in detail below with reference to the drawings. It should be understood that, the specific embodiments described herein are only used for describing and explaining the present invention, rather than limiting the present invention.

In the present invention, unless specifically stated to the contrary, used directional terms such as "inside" and "outside" are defined by a human body during a treatment.

As shown in FIG. 1 to FIG. 4, the present invention provides a guidewire-guiding device and a guidewire-guiding assembly using the device. Wherein, the guidewire-guiding device includes a guiding body 1, for the convenience of being embedded in vivo without generating injury to the human body, preferably, the section of the guiding body 1 is circular, and thus obtain a better safety performance. Wherein, the guiding body 1 may be made of polytetrafluoroethylene and other materials, and its axial length may be determined according to different operation requirements.

Wherein, in order to achieve the objectives of the present invention, a main guidewire channel 2 and guidewire-guiding channels 3 are respectively formed in the guiding body 1, the main guidewire channel 2 and the guidewire-guiding channels 3 respectively penetrate through the guiding body 1 along an axial direction, and in-vivo end openings of the guidewire-guiding channels 3 and the in-vivo end opening of the main guidewire channel 2 are arranged along the axial direction at intervals. In addition, the guidewire-guiding assembly provided by the present invention includes the above guidewire-guiding device, and a guidewire catcher 5 stretching in from the in-vitro end openings of the guidewire-guiding channels 3 and stretching out from the in-vivo end openings.

Therefore, in the above technical solution of the present invention, the guiding body 1 may be imbedded into a blood vessel in vivo via a main guidewire 4 penetrating through the main guidewire channel 2, and to-be-guided guidewires, for example, branch guidewires 6 of branch blood vessels, may be guided into the guidewire-guiding channels 3 via the guidewire catcher 5. As the in-vivo end openings of the guidewire-guiding channels 3 are arranged along the axial direction at intervals, the to-be-guided guidewires may enter the guidewire-guiding channels 3 while being staggered to the main guidewire 4 on the axial direction, therefore the problem of tanglement of the main guidewire 4, the branch guidewires 6 and other kinds of guidewires can be avoided, furthermore, the to-be-guided guidewires may be conveniently guided into the guiding body 1 via the guidewire catcher 5, accordingly the operation is convenient, and the practicability is high.

Wherein, the guidewire catcher 5 used in the present invention is a common component in the art. For example, in the present embodiment, the guidewire catcher 5 may be a catcher with a model number CloverSnare® 4-Loop Vascular Retriever (intravascular catcher), produced by the American COOK company. In other embodiments, any catcher capable of guiding the guidewires should fall within the protection scope of the present invention. In addition, the main guidewire 4 used in the present invention for embedding the guiding body 1 into the blood vessel in vivo may be an additional component and may also be a main guidewire, for example, an intravascular stent embedding system, in the interventional therapy.

In order to guide more guidewires, in the present embodiment, multiple guidewire-guiding channels 3 are arranged, and the in-vivo end openings of the plurality of guidewire-guiding channels are arranged along the axial direction at intervals. This may ensure that all the guidewires in the operation are guided. As an example, three guidewire-guiding channels 3 are arranged to correspond to the branch guidewires 6 in three branch blood vessels 10 respectively. Wherein, the specific number of the guidewire-guiding channels 3 in the present invention may be determined according to the number of the guidewires used in the operation, such as three, four or more.

In addition, as shown in FIG. 2, in the present embodiment, in-vitro end openings of the plurality of guidewire-guiding channels 3 and the main guidewire channel 2 are arranged at equal intervals along the circumferential direction of the guiding body 1. Therefore, a plurality of guidewires led out from the guiding body 1 may be arranged neatly so as to be conveniently connected to the corresponding in-vitro end control device. As the in-vivo end openings of the plurality of guidewire-guiding channels 3 and the main guidewire channel 2 are arranged along the axial direction at intervals, a part of the guidewire-guiding channels 3 are arranged in the guiding body 1 in a curved shape. Since the channels are separated from one another, and the guidewires have flexibility, the functions of the guidewires are not affected even if they are bent in the guiding body 1, and meanwhile the guidewires are not tangled.

As shown in FIG. 1, in order to form the ports along the axial direction at intervals on the in-vivo ends, in a first embodiment of the present invention, an in-vivo end face 11 of the guiding body 1 is formed into a diagonal plane, and the main guidewire channel 2 and the guidewire-guiding channels 3 are arranged along the diagonal plane to be separated on the axial direction. In the case of the plurality of guidewire-guiding channels 3, the in-vivo end openings of the plurality of guidewire-guiding channels 3 and the main guidewire channel 2 may be arranged along the center line of the diagonal plane, wherein when the section of the guiding body 1 is circular, the diagonal plane is oval, and thus the plurality of in-vitro end openings may be arranged along the long axis of the oval. In addition, the plurality of in-vitro end openings may also be arranged along different lines according to needs. Due to this diagonal plane, a plurality of channel openings may be conveniently arranged, and the movement of the guiding body 1 in vivo is also facilitated for guiding. Furthermore, Due to the diagonal plane, the plurality of channel openings may also be deployed along the radial direction or the tangential direction while being deployed along the axial direction, therefore the plurality of guidewires may be more easily separated from one other before entering the guiding body 1 without tangling.

As shown in FIG. 3, in a second embodiment of the present invention, instead of the integral diagonal plane in FIG. 1, the in-vivo end face 11 of the guiding body 1 in the present embodiment is formed into a plurality of diagonal planes shaping as a step structure, the plurality of diagonal planes are parallel, and the main guidewire channel 2 and the guidewire-guiding channels 3 are respectively formed on different diagonal planes. Specifically, four diagonal planes may be formed, and meanwhile four in-vivo end openings of one main guidewire channel 2 and three guidewire-guiding channels 3 are formed. This arrangement mode of the plurality of diagonal planes may also achieve the objective of separating the plurality of channel openings from one another and ensuring no tangling of the guidewires before entering the guiding body 1.

In the embodiment of the present invention, in order to facilitate the manufacturing of the guidewire-guiding device, preferably, the main guidewire channel 2 and the guidewire-guiding channels 3 are respectively formed by pipelines 8 and are coated in the guiding body 1. As shown in FIG. 1, one pipeline 8 is shown by a dotted line. In other words, the guidewire-guiding device provided by the present invention may be formed by coating and fixing a plurality of independent pipelines 8 via a coating material. In other possible embodiments, the guidewire-guiding device provided by the present invention may also be manufactured by integrally forming a through hole in the guiding body 1, as the process allows.

As shown in FIG. 4, in a third embodiment of the present invention, different from the first and second embodiments, the pipelines 8 forming the main guidewire channel 2 and the guidewire-guiding channels 3 respectively protrude from the in-vivo end face of the guiding body 1. That is to say, the in-vivo end openings of the plurality of channels are not formed in the in-vivo end face of the guiding body 1, but are freely arranged with the in-vivo end openings of the pipelines 8 with different lengths, in this way, the introduction of the guidewires is achieved, and the tanglement of the guidewires is prevented as well.

In the present embodiment, a development marking line 7 extending along the axial direction is arranged on the guiding body 1 for the convenience of operation. Wherein the development marking line 7 may be observed in real time during the operation, in this way, reference is provided for the operation depending on the position and the degree of deformation of the development marking line 7, and thus the operation is more accurate. In the second embodiment provided by the present invention, the development marking line 7 includes an integral segment 71 and a plurality of sub-segments 72, the integral segment 71 is arranged on an outer side wall of the guiding body 1, the plurality of sub-segments 72 are respectively arranged on a plurality of step surfaces of the step structure and may be formed on a connecting line between adjacent in-vivo end openings, and the step surfaces are located between the adjacent diagonal planes and are parallel to one another. In this way, in addition to the function of the integral segment 71, the positions of the channel openings may also be marked under the assistance of the plurality of sub-segments 72, so that the operation is more accurate and quicker.

In addition, preferably, the in-vivo end openings of the guidewire-guiding channels 3 and/or the main guidewire channel 2 are trumpet-shaped, the trumpet-shape is a structure that opens toward the outer side of each channel, the trumpet-shaped design may allow the introduction of the guidewires through the large-opening segment, and the guidewires are stably guided via a small diameter segment, such that the operation is more convenient. Accordingly, the introduction of the guidewires is facilitated.

In addition, in order to guide a plurality of guidewires, in the present embodiment, the in-vivo end opening of the main guidewire channel 2 is arranged in the vicinity of the long axis of the oval, for example, the inner most end of the guiding body 1, and in this case, the guidewire-guiding channels 3 may be arranged along the long axis in sequence. In addition, in the present embodiment, the main guidewire channel is used for guiding a main guidewire 4 penetrating through a main blood vessel 9, and the guidewire-guiding channels are used for guiding branch guidewires 6 penetrating through branch blood vessels 10 connected to the main blood vessel. Therefore, the main guidewire 4 may be arranged close to the side wall of the main blood vessel 9, and the diagonal plane may face the openings of the plurality of branch blood vessels 10 connected to the main blood tube 9, thereby being more conducive to guiding the branch guidewires 6 into the guiding body 1. The guidewires are arranged more orderly to avoid tangling.

A guidewire-guiding method provided by the present invention will be described below, wherein the above-mentioned guidewire-guiding assembly provided by the present invention is used in the guidewire-guiding method, and the guidewire-guiding method includes: a, embedding the main guidewire 4 to a predetermined position; specifically the manner of embedding the main guidewire 4 is the same as that of embedding the guidewires of such as intravascular stent and the like in interventional surgery; b, penetrating the main guidewire 4 into the main guidewire channel 2, and embedding the guiding body 1 in vivo along the main guidewire 4; therefore, the main guidewire 4 may guide the guiding body 1; c, penetrating the guidewire catcher 5 into the guidewire-guiding channels 3 and extending out from the in-vivo end openings to catch to-be-guided guidewires 6; in this step, the guidewire catcher 5 may be embedded into the guidewire-guiding channels 3 in advance and extend out after the guiding body 1 moves to a specified position, and the guidewire catcher 5 may also be embedded after the guiding body 1 moves to a braking position; and finally d, pulling the guidewire catcher 5 to guide the to-be-guided guidewires 6 into the guidewire-guiding channels 3. In this way, the surgical guidewires, in particular the main guidewire 4 and the branch guidewires 6, are guided by the guiding body 1 to extend in vitro, the in-vitro ends of the guidewires can extend out from the in-vitro end openings of the guidewire-guiding channels 3 to be connected with the corresponding operating devices. In this way, by means of the embedded guiding body 1, all kinds of guidewires used in the operation may be arranged in vivo in a better sequence for extending without generating the problem of tangling and so on, and thus smooth operation is achieved.

Although the preferred embodiment of the present invention have been described above in detail in combination with the drawings, the present invention is not limited to the specific details in the above embodiments. Various simple modifications may be made to the technical solutions of the present invention within the scope of the technical concept of the present invention, and these simple variations all belong to the protection scope of the present invention.

In addition, it should be noted that, the specific technical features described in the foregoing specific embodiments may be combined in any suitable manner without any contradiction. In order to avoid unnecessary repetition, various possible combinations are not additionally described in the present invention.

In addition, various different embodiments of the present invention may also be randomly combined, and the combination should also be regarded as the disclosure of the present invention as long as it does not violate the spirit of the present invention.

The invention claimed is:

1. A guidewire-guiding device, comprising a guiding body, wherein a main guidewire channel and a plurality of guidewire-guiding channels are respectively arranged in the guiding body, the main guidewire channel and the plurality of guidewire-guiding channels respectively penetrate through the guiding body along an axial direction, and when placed inside a body, in-vivo end openings of the plurality of guidewire-guiding channels and an in-vivo end opening of the main guidewire channel are arranged along the axial direction at intervals,
    wherein an in-vivo end face of the guiding body is formed as a step structure, which has a plurality of diagonal planes, each of the plurality of diagonal planes is parallel to the others, a section of the guiding body is circular, outside edges of the plurality of diagonal planes on a periphery of the guiding body could be joined into an oval, and the in-vivo end opening of the main guidewire channel and the in-vivo end openings of the plurality of guidewire-guiding channels are respectively formed on different diagonal planes of the plurality of diagonal planes, and wherein the in-vivo end opening of the main guidewire channel and the in-vivo end openings of the plurality of guidewire-guiding channels are arranged along a long axis and all of the in-vivo end openings of the plurality of guidewire-guiding channels are arranged at a same side of the in-vivo end opening of the main guidewire channel.

2. The guidewire-guiding device of claim 1, wherein the main guidewire channel and the plurality of guidewire-guiding channels are respectively formed by pipelines and are coated by the guiding body.

3. The guidewire-guiding device of claim 2, wherein the pipelines of the main guidewire channel and the plurality of guidewire-guiding channels respectively protrude from the in-vivo end face of the guiding body.

4. The guidewire-guiding device of claim 1, wherein a development marking line extending along the axial direction is arranged on the guiding body.

5. The guidewire-guiding device of claim 1, wherein a development marking line extending along the axial direction is arranged on the guiding body, the development marking line comprises an integral segment and a plurality of sub-segments, the integral segment is deployed on an outer side wall of the guiding body, the plurality of sub-segments are respectively deployed on a plurality of step surfaces of the step structure and are formed on a connecting line between adjacent in-vivo end openings of the plurality of guidewire-guiding channels and the in-vivo end opening of the main guidewire channel, and the plurality of step surfaces are located between adjacent diagonal planes of the plurality of diagonal planes and are parallel to one another.

6. The guidewire-guiding device of claim 1, wherein the in-vivo end openings of the plurality of guidewire-guiding channels and/or the in-vivo end opening of the main guidewire channel is/are trumpet-shaped.

7. The guidewire-guiding device of claim 1, wherein the main guidewire channel is configured to guide a main guidewire penetrating through a main blood vessel, and the plurality of guidewire-guiding channels are configured to guide branch guidewires penetrating through branch blood vessels connected to the main blood vessel.

* * * * *